United States Patent
Itoh

(10) Patent No.: US 7,485,264 B2
(45) Date of Patent: Feb. 3, 2009

(54) TEST TUBE HOLDER

(75) Inventor: Teruaki Itoh, Kumamoto (JP)

(73) Assignee: IDS Company, Ltd., Kumamoto (JP)

( * ) Notice: Subject to any disclaimer, the term of this patent is extended or adjusted under 35 U.S.C. 154(b) by 877 days.

(21) Appl. No.: 11/079,291

(22) Filed: Mar. 15, 2005

(65) Prior Publication Data

US 2005/0207945 A1  Sep. 22, 2005

(30) Foreign Application Priority Data

Mar. 17, 2004  (JP) .................... 2004-075947

(51) Int. Cl.
*B01L 9/00* (2006.01)
*B01L 9/06* (2006.01)
(52) U.S. Cl. .................... 422/104; 422/99; 422/102; 206/443; 211/60.1
(58) Field of Classification Search .............. 422/99, 422/102, 104; 211/60.1; 206/443
See application file for complete search history.

(56) References Cited

U.S. PATENT DOCUMENTS

| 1,594,792 A | * | 8/1926 | Mortimer | .................... 294/99.2 |
| 6,274,092 B1 | * | 8/2001 | Itoh | ........................... 422/104 |
| 6,971,506 B2 | * | 12/2005 | Hassinen et al. | ....... 198/803.14 |
| 2003/0133848 A1 | * | 7/2003 | Itoh | ........................... 422/104 |
| 2003/0161764 A1 | * | 8/2003 | Itoh | ........................... 422/104 |
| 2003/0215370 A1 | * | 11/2003 | Itoh | ........................... 422/104 |

FOREIGN PATENT DOCUMENTS

JP    2003-211006    7/2003
WO    WO 96/36437   11/1996

* cited by examiner

*Primary Examiner*—Jill Warden
*Assistant Examiner*—Paul S Hyun
(74) *Attorney, Agent, or Firm*—Nixon & Vanderhye P.C.

(57) ABSTRACT

A test tube holder includes a main body and an adapter. The main body includes a cylindrical hollow portion for accommodating a test tube. The adapter is provided in the cylindrical hollow portion to hold the test tube. The adapter includes bottom portions, holding portions and loop portions, which are U-shaped as a whole. The bottom portions are located to cross the center axis of the cylindrical hollow portion. The loop portions are provided at the ends of the bottom portions, and coiled at least one. The holding portions are continuous with the loop portions and the bottom portions. The bottom portions of first and second spring steel wires are provided in the cylindrical hollow portion to intersect with each other. The holding portions of the first and second spring steel wires are projected upwards from the cylindrical hollow portion.

3 Claims, 2 Drawing Sheets

TEST TUBE HOLDER

CROSS-REFERENCE TO RELATED APPLICATIONS

This application is based upon and claims the benefit of priority from prior Japanese Patent Application No. 2004-075947, filed Mar. 17, 2004, the entire contents of which are incorporated herein by reference.

BACKGROUND OF THE INVENTION

1. Field of the Invention

This invention relates to a test tube holder for use in carriage of a test tube containing a specimen such as blood.

2. Description of the Related Art

A test tube containing a specimen such as blood is formed of transparent glass or plastic. A cap formed of rubber or synthetic resin is put on an upper opening portion of the test tube. The test tube is carried to each of processing sections, while being vertically held by a test tube holder and guided along a carrier passage, in order that the specimen contained in the test tube be served or poured into another test tube.

Therefore, the test tube holder is formed to stably and vertically hold each of kinds of test tubes having different lengths and diameters, when each test tube is carried. The test tube holder has a base body constituting a holder body. The base body is formed rotation-symmetrically with respect to an axis extending along a vertical direction. Furthermore, an engaging portion provided at an outer peripheral surface of a proximal end portion of the base body. The engaging portion is engaged with a guide rail of a conveying system. A cylindrical hollow portion for accommodating a test tube is provided in a center portion of the base body to extend from an upper end of the base body to a predetermined depth toward a proximal end of the base body. Furthermore, Jpn. Pat. Appln. KOKAI Publication No. 2003-211006 discloses a test tube holder providing with an adapter which enables a test tube having a diameter falling within a given diameter range to be inserted into the test tube holder, and which is provided in a cylindrical hollow portion of a holder body.

In particular, it should be noted that the test tube holder disclosed in Jpn. Pat. Appln. KOKAI Publication No. 2003-211006 has a plurality of leaf springs provided in the cylindrical hollow portion of the holder body. The leaf springs have contact portions which contact the outer peripheral surface of a test tube to be held. The test tube holder includes one O-ring which bundles the leaf springs in such a way as to surround them, in order that the contact portions press the outer peripheral surface of the test tube at a given pressure.

In the above test holder, the elasticity of the leaf springs is compensated for by the O-ring, and the structures of the leaf springs and peripheral members thereof are complicated. Thus, the parts of the test holder cannot be easily assembled, as a result of which the manufacturing cost is increased, and the maintenance is troublesome when the O-ring is damaged or broken.

BRIEF SUMMARY OF THE INVENTION

The present invention provides a test tube holder which has a simpler structure, can be more easily assembled from parts, and has a high durability.

A test tube holder according to the present invention comprises a main body and an adapter. The main body includes a cylindrical hollow portion for accommodating a test tube. The adapter is provided in the cylindrical hollow portion to hold the test tube. The adapter includes first and second spring steel wires, which have bottom portions, loop portions and holding portions, and which are U-shaped as a whole. The bottom portions are located to cross the center of the cylindrical hollow portion. The loop portions are provided at the both ends of the bottom portions, and are coiled at least one. The holding portions continuously extend upwards from the loop portions and the bottom portion. The bottom portions of the first and second spring wire steels are provided in the cylindrical hollow portion in such a way as to intersect with each other. The holding portions of the first and second spring wire steels are projected upwards from the cylindrical hollow portion.

In this case, a spacer is further provided in the cylindrical hollow portion, and includes engagement grooves in which the holding portions of the first and second spring steel wires are fitted. The holding portions of the first and second spring steel wires are held at regular intervals in the circumferential direction of the cylindrical hollow portion.

Furthermore, at upper end portions of the holding portions of the first and second spring steel wires, guiding portions are provided and warped outwards from the cylindrical hollow portion.

In the test tube holder according to the present invention, the structure for holding each of test tubes having different lengths and outer diameters is simple. Accordingly, parts of the test tube holder can be more easily assembled, thus reducing the manufacturing cost. Furthermore, the durability of the test tube holder is improved.

Additional advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Figure 1:
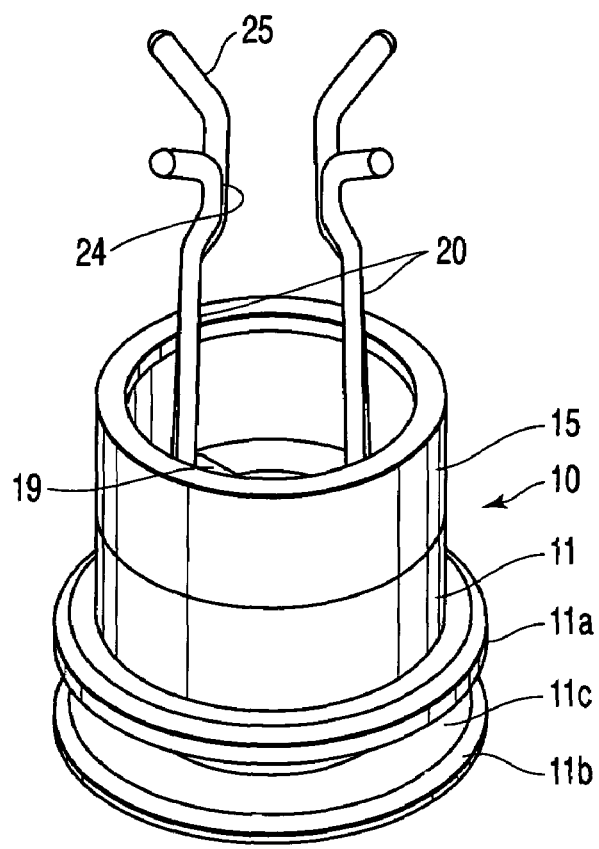
FIG. 1 is a perspective view of a test tube holder according to the first embodiment of the present invention.
Figure 2:
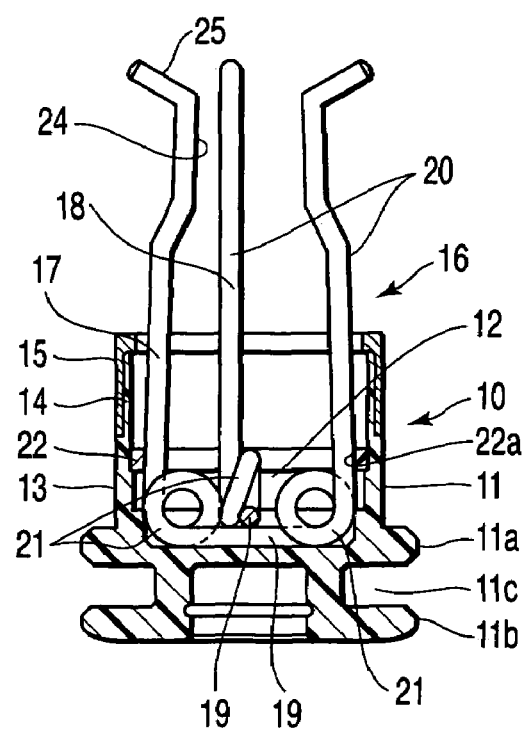
FIG. 2 is a vertical section of the test tube holder in FIG. 1.
Figure 3:
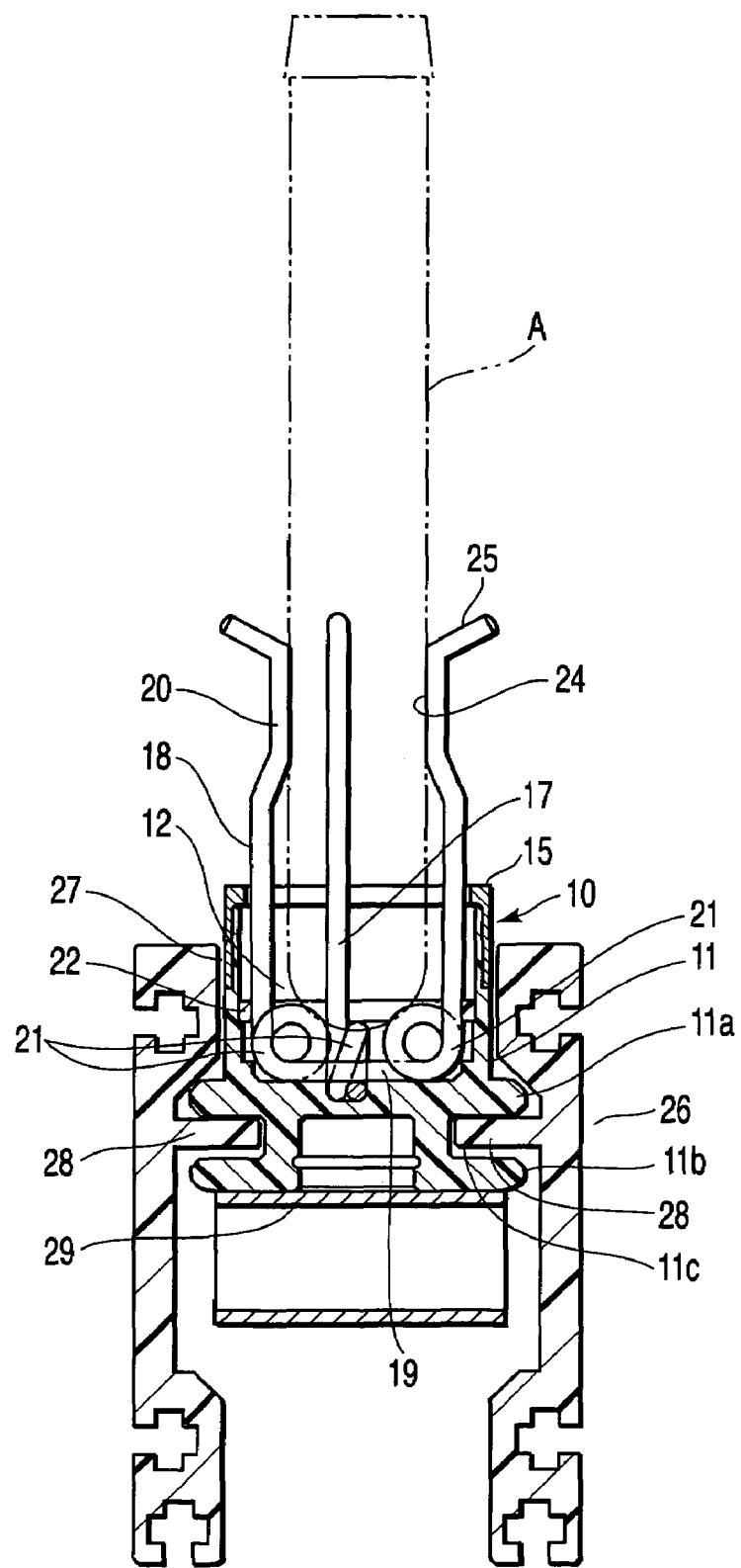
FIG. 3 is a vertical section of the test tube holder which is moved over a conveyor rail, with a test tube inserted in the test tube holder.

A test tube holder 1 according to an embodiment of the present invention will be explained with reference to FIGS. 1 to 3. The test tube holder 1 has a main body 10 and an adapter 16. The main body 10 is formed of a synthetic resin material. Flange portions 11a and 11b are formed at an outer peripheral surface of a proximal end portion of a cylindrical base body 11 of the main body 10. They are vertically arranged at two stages. Therefore, an annular groove 11c is provided between the flange portions 11a and 11b. As shown in FIG. 3, convex portions 28 of a conveyor rail 26 are fitted in the annular groove 11c between the flange portions 11a and 11b.

A cylindrical hollow portion 12 for accommodating a test tube is formed in a center portion of the cylindrical base body 11 to extend from an upper end portion thereof to a depth corresponding to the position of the flange portion 11a at the upper stage. A central portion of the cylindrical base body 11 in the longitudinal direction thereof is provided as a large-diameter portion 13, and a distal end portion of the cylindrical base body 11, which is continuous with the large-diameter portion 13, is provided as a small-diameter portion 14. A metal ring 15 is engaged with the small-diameter portion 14. The metal ring 15 serves as an indicating portion to detect the presence of the test tube by a detector. The detector is of an optical type or a magnetic type.

The adapter 16 is provided in the cylindrical hollow portion 12, and holds a test tube A which contains a specimen such as collected blood, and is formed of transparent glass or plastic. The adapter 16 comprises a first spring steel wire 17, a second spring steel wire 18 and a spacer 22.

The first spring steel wire 17 includes a bottom portion 19, holding portions 20 and loop portions 21, which are continuously formed in a U-shape as a whole. The holding portions 20 extend upwards from the both sides of the bottom portion 19. The loop portions 21 are formed to continuously extend between the bottom portion 19 and the holding portions 20, and to be coiled one and a quarter or two and a quarter. Due to provision of the loop portions 21, the upper ends of the holding portions 20 are warped in a direction toward or away from the center of the tube holder. Basically, the second spring steel wire 18 has the same shape as the first spring steel wire 17.

The spacer 22 is provided in the cylindrical hollow portion 12, and is ring-shaped in such a way as tightly contact an inner peripheral surface of the cylindrical hollow portion 12. In an inner peripheral surface of the spacer 22, engagement grooves 22a are arranged at intervals of 90° in a circumferential direction. The first spring steel wire 17 and the second spring steel wire 18 are engaged with the engagement grooves 22a in positions close to proximal portions of the holding portions 20, thereby maintaining their positional relationship. The bottom portion 19 of the first spring steel wire 17 crosses the bottom portion 19 of the second spring steel wire 18. To be more specific, in the embodiment, the bottom portion 19 of the second spring steel wire 18 is stacked on the bottom portion 19 of the first spring steel wire 17. The holding portion 20 of the first spring steel wire 17 is formed to be longer than the holding portion 20 of the second spring steel wire 18 by the diameter of each of the first and second spring steel wires 17 and 18, so that the height of the holding portion 20 of the first spring steel wire 17 is equal to that of the holding portion 20 of the second spring steel wire 18.

The holding portions 20 project more upwards than the cylindrical hollow portion 12. Pressure-contacting portions 24 and guiding portions 25 are provided at the projected holding portions 20. The pressure-contacting portions 24 are warped toward a center axis of the test tube holder 1 to contact the outer peripheral surface of the test tube A. The guiding portions 25 are provided at the upper ends of the holding portions 20, and are formed to be continuous with the pressure-contacting portions 24 and to be bent in a direction away from the center axis. When the test tube A is inserted into the test tube holder 1 from above, the guiding portions 25 guide the test tube A such that it is located between the holding portions 20.

The test tube holder 1 having the above structure is engaged with the conveyor rail 26 as shown in FIG. 3, and conveys the test tube A while vertically holding the test tube A. The conveyor rail 26 comprises a conveyor passage 27, the convex portions 28 and a conveyor belt 29. The conveyor passage 27 has a width which is slightly greater than the outer diameter of the main body 10 of the test tube holder 1. The convex portions 28 continuously extend along the extending direction of the conveyor rail 26, and are provided at inner side surfaces of the conveyor passage 27 to have the same height. The convex portions 28 are fitted in the annular groove 11c provided in the test tube holder 1.

The conveyor belt 29 is an endless hoop provided in the conveyor passage 27 in the carrying direction of the conveyor rail 26, and circulates such that it conveys the test tube A on its upper side, and it returns on its lower side. A bottom surface of the main body 10 of the test tube holder 1 contacts an upper surface of the conveyor belt 29. Due to friction of the conveyor belt 29 with the bottom surface of the test tube holder 1, the test tube holder 1 is moved along the conveyor passage 27 when the conveyor belt 29 is moved.

The test tube holder 1 comprises the main body 10 and the adapter 16. The adapter 16 comprises the first spring steel wire 17, the second spring steel wire 18, and the spacer 22. The bottom portion 19 of the first spring steel wire 17 and the bottom portion 19 of the second spring steel wire 18 cross over each other in the cylindrical hollow portion 12, and the holding portions 20 are formed to project upwards from the cylindrical hollow portion 12.

In such a manner, the number of parts of the test tube holder 1 is small, and they are easily assembled, thus reducing the manufacturing cost. Furthermore, the holding portions 20 have the guiding portions 25 at their upper end portions, which are warped outwards from the center of the test tube holder 1, thereby enabling the test tube A to be more easily inserted from above into the cylindrical hollow portion 12.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A test tube holder comprising:
   a main body including a cylindrical hollow portion for accommodating a test tube; and
   an adapter provided in the cylindrical hollow portion, for holding the test tube, the adapter including first and second spring steel wires which include: bottom portions located to cross a center of the cylindrical hollow portion; loop portions provided at ends of the bottom portions, and coiled at least once; and holding portions extending upwards continuous with the loop portions and the bottom portions, the first and second spring steel wires being U-shaped as a whole,
   wherein the bottom portions of the first and second spring steel wires are provided in the cylindrical hollow portion such that the bottom portions of the first and second spring steel wires intersect with each other, and the holding portions of the first and second spring steel wires are projected upwards from the cylindrical hollow portion.

2. A test tube holder according to claim 1, further comprising a spacer including engagement grooves in which the holding portions of the first and second spring steel wires are fitted, and which hold the holding portions of the first and second spring steel wires at regular intervals in a circumferential direction of the cylindrical hollow portion.

3. The test tube holder according to claim 1, wherein the holding portions of the first and second spring steel wires include respective guiding portions which are formed at upper end portions of the holding portions of the first and second spring steel wires, and which are warped outwards from the cylindrical hollow portion.

* * * * *